United States Patent [19]

Arndt et al.

[11] 4,316,861

[45] Feb. 23, 1982

[54] N-NITROARYL-N-HALOSULFONYL UREAS

[75] Inventors: Otto Arndt; Wolfgang Tronich, both of Hofheim am Taunus, Fed. Rep. of Germany

[73] Assignee: Hoechst Aktiengesellschaft, Frankfurt am Main, Fed. Rep. of Germany

[21] Appl. No.: 105,560

[22] Filed: Dec. 20, 1979

[30] Foreign Application Priority Data

Dec. 23, 1978 [DE] Fed. Rep. of Germany ....... 2855884

[51] Int. Cl.³ .......................................... C07C 143/70
[52] U.S. Cl. ............................ 260/543 F; 260/543 R; 260/465 D; 564/50
[58] Field of Search ............ 260/543 R, 543 F, 465 D

[56] References Cited

U.S. PATENT DOCUMENTS 3,996,208 12/1976 Fechtig et al. ........................ 544/22

FOREIGN PATENT DOCUMENTS 872670 7/1961 United Kingdom ............ 260/543 R

*Primary Examiner*—Paul J. Killos
*Attorney, Agent, or Firm*—Curtis, Morris & Safford

[57] ABSTRACT

N-o-nitro-phenyl- or -naphthyl-N'-halogensulfonyl ureas which may be substituted in their aromatic rings by a further nitro group (and the phenyl ureas also by fluoro, chloro, bromo, lower alkyl, lower alkoxy, trifluoromethyl, cyano or phenyl) are obtained by reacting the corresponding o-nitraniline with fluoro- or chlorosulfonylisocyanate. The products can be hydrolyzed to yield the corresponding nitroaryl ureas.

4 Claims, No Drawings

N-NITROARYL-N-HALOSULFONYL UREAS

One embodiment of the present invention is N-nitroaryl-N'-halosulfonyl ureas of the formula I

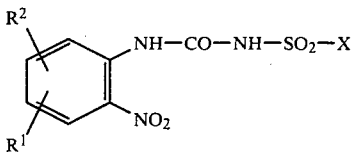

in which X is fluorine or chlorine, $R^1$ is hydrogen or nitro and $R^2$ is hydrogen, fluorine, chlorine, bromine, lower alkyl, lower alkoxy, trifluoromethyl, cyano, phenyl or a fused benzene ring.

In preferred compounds of the invention X stands for chlorine and $R^2$ represents hydrogen, chlorine, methyl, methoxy, cyano or a fused benzene ring.

Another embodiment of the invention is a process for the preparation of the compounds of formula I, which comprises reacting an amine of the formula II

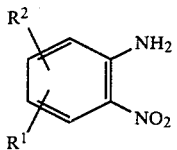

in which $R^1$ and $R^2$ are defined as above, with fluoro- or preferably chlorosulfonyl isocyanate, advantageously in an inert organic solvent.

A further subject of the invention is the use of the compounds of formula I for the preparation of the corresponding nitroaryl ureas of the formula III

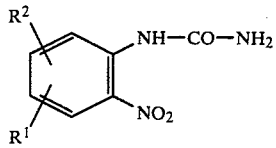

in which $R^1$ and $R^2$ are defined as above, by way of hydrolysis.

In the following, further preferred embodiments of the invention are described in detail.

The reaction of an amine of formula II with a halosulfonyl isocyanate may be carried out without solvent or diluent, especially in the case of liquid amines; however, the said substances are preferably reacted in an inert solvent or diluent, the amine of formula II either being suspended or dissolved in this reaction medium.

Suitable solvents or diluents are all liquids which are inert towards the reactants, such as aliphatic and aromatic unsubstituted or substituted hydrocarbons or heterocyclic compounds, for example tetramethylene sulfone or cyclic ethers. Preference is given to aromatic hydrocarbons, such as xylenes, chlorobenzene, dichlorobenzenes, and especially toluene. If there are used aqueous solvents or diluents or amines, a dehydration, for example by way of azeotropic distillation, must naturally be effected prior to the reaction with the halosulfonyl isocyanate.

The halosulfonyl isocyanate is preferably employed in a small excess amount.

The reaction temperature is preferably in the range between room temperature and the boiling point of the solvent or diluent employed, particularly between 40° and 100° C. Depending on the reaction temperature, the reaction period is generally from 2 to 20 hours.

The product of the formula I can be isolated from the reaction medium, preferably at relatively low temperatures, and may be washed with the reaction medium or another inert solvent. It may be identified, for example, by way of the nuclear magnetic resonance spectra.

For use according to the invention of the product an isolation is not required, however, and does not involve any advantages, since the product is sensitive to moisture. The product is therefore preferably hydrolyzed without isolation to give the corresponding nitroaryl ureas. By way of this saponification to give the aryl urea the products may also be identified.

The saponification is preferably effected by adding water to the reaction mixture, generally at a temperature of less than 25° C. The saponification is carried out at a temperature of from about 10 to about 100° C., preferably at 50° to 80° C.; however, other saponification temperatures are possible as well.

The saponification time depends on the saponification temperature, and is generally in the range of from 3 to 5 hours.

The hydrolysis may be effected at a pH in the range of from about 1 to 9, the acid range being preferred.

The nitroaryl urea may be isolated, for example by filtration, directly from the reaction mixture or following a previous neutralization of the hydrohalic acid and sulfuric acid formed. It is also possible, however, to eliminate first the organic solvent from the neutralized suspension, for example by way of distillation with steam. Said organic solvent may then be used several times for the process of the invention either in a regenerated form or as a mother liquor.

The compounds of the invention are suitable for a great number of further reactions, due to the reactive halosulfonyl group. It is advantageous that these secondary products contain one or two nitro groups as further functional group(s), said nitro group(s) making the secondary products appropriate for a variety of purposes, either directly or following the conversion of the nitro groups into amino groups.

With the use according to the invention there are obtained known nitroaryl ureas. These compounds may be converted into the mono- and diaminophenyl or -naphthyl ureas by way of reduction, in particular a catalytic hydrogenation, of the nitro groups, and from said urea compounds the corresponding benzimidazolones or naphthimidazolones may be prepared by cyclization, while splitting off ammonia. When starting from dinitroaryl ureas, amino benzimidazolones or aminonaphthimidazolones are thus obtained in an easy manner; these may be used as diazo components and as coupling components for azo pigments following a reaction, for example with diketene, to give the N-acetoacetyl compound.

In the following Examples, the parts and percentages relate to the weight, unless otherwise stated.

EXAMPLE 1

311 Parts of 2,4-dinitroaniline are stirred in 2600 parts of toluene with 312 parts of chlorosulfonyl isocyanate for 4 hours at 80° C. At 25° C., 360 parts of water are added to the resulting suspension of N-2,4-dinitrophenyl- N'-chlorosulfonyl urea without intermediate isolation of the latter, and the mixture obtained is saponified at 60° C. within 4 hours to yield 2,4-dinitrophenyl urea. After diluting it with water, the mixture is filtered, while hot, and the product is washed with hot toluene and water. After drying in vacuo, there are obtained 347 parts of 2,4-dinitrophenyl urea having a melting point of from 195° to 197° C.

EXAMPLE 2

370 Parts of 6-chloro-2,4-dinitroaniline are stirred for 4 hours at 80° C. in 2600 parts of toluene with 312 parts of chlorosulfonyl isocyanate. At 25° C., 360 parts of water are added to the resulting suspension of N-6-chloro-2,4-dinitrophenyl-N'-chlorosulfonyl urea without intermediate isolation, and the mixture is saponified at 60° C. within 4 hours to yield 6-chloro-2,4-dinitrophenyl urea. After diluting said mixture with water, it is neutralized with 33% sodium hydroxide solution, filtered while hot, and the product is thoroughly washed with hot toluene and water. After drying in vacuo, there are obtained 383 parts of 6-chloro-2,4-dinitrophenyl urea having a melting point of from 219° to 221° C.

EXAMPLE 3

The process is carried out according to the specifications given in Example 2, with the exception that the reaction is carried out in 3000 parts of toluene mother liquor. The work-up and isolation of the final product are effected according to Example 2. After drying in vacuo, there are obtained 426 parts of 6-chloro-2,4-dinitrophenyl urea having a melting point of from 213° to 215° C.

EXAMPLE 4

The process is carried out as has been described in Example 2, with the exception that the suspension of the N-6-chloro-2,4-dinitrophenyl-N'-chlorosulfonyl urea formed is filtered off at room temperature and washed with toluene. The chlorosulfonyl urea thus isolated intermediately is subsequently introduced into 7000 parts of water at 50° C., while stirring. Thereafter 600 parts of sodium hydrogencarbonate are slowly introduced, while stirring, also at 50° C. In the course of this process the chlorosulfonyl urea is saponified within 3 hours. The 6-chloro-2,4-dinitrophenyl urea is filtered off and is washed with 2000 parts of water of 50° C.

EXAMPLE 5

40 of 6-methyl-2,4-dinitroaniline are stirred for 4 hours at 80° C. in 500 parts of toluene with 34 parts of chlorosulfonyl isocyanate. The suspension of the chlorosulfonyl urea obtained is mixed at 25° C. with 40 parts of water and saponified at 60° C. to give 6-methyl-2,4-dinitrophenyl urea.

The product is worked up and isolated as has been described in Example 2. After drying in vacuo, there are obtained 34 parts of 6-methyl-2,4-dinitrophenyl urea having a melting point of from 216° to 218° C.

EXAMPLE 6

The reaction corresponds to Example 5, with the exception that 5-methyl-2,4-dinitroaniline is employed instead of 6-methyl-2,4-dinitroaniline. There are obtained 42 parts of 5-methyl-2,4-dinitrophenyl urea having a melting point of from 186° to 188° C.

EXAMPLE 7

641 Parts of 5-methoxy-2,4-dinitroaniline are stirred for 4 hours at 80° C. in 3500 parts of toluene with 510 parts of chlorosulfonyl isocyanate. The resulting chlorosulfonyl urea is saponified at 25° C., after 450 parts of water have been added. The final product is worked up and isolated according to the specifications given in Example 2. After drying in vacuo, there are obtained 758 parts of 5-methoxy-2,4-dinitrophenyl urea having a melting point of from 212° to 215° C.

EXAMPLE 8

234 Parts of 2,4-dinitro-naphthylamine are stirred for 6 hours at 80° C. in 3500 parts of toluene with 213 parts of chlorosulfonyl isocyanate. The suspension of the chlorosulfonyl urea formed is mixed with 250 parts of water at 25° C. and saponified within 4 hours at 60° C. The final product is worked up and isolated as has been described in Example 2. There are obtained 237 parts of 2,4-dinitronaphthyl urea having a melting point of from 214° to 216° C.

EXAMPLE 9

275 Parts of 2,6-dinitroaniline are stirred for 8 hours at 80° C. in 2750 parts of toluene with 319 parts of chlorosulfonyl isocyanate. The suspension of the resulting chlorosulfonyl urea is mixed with 375 parts of water at 25° C. and saponified at 60° C. The final product is worked up and isolated according to the specifications given in Example 2. After drying in vacuo, there are obtained 305 parts of 2,6-dinitrophenyl urea having a melting point of from 215° to 217° C.

EXAMPLE 10

28 Parts of 2-nitroaniline are stirred for 4 hours at 80° C. in 550 parts of toluene with 34 parts of chlorosulfonyl isocyanate. At 25° C., 40 parts of water are added to the suspension of the chlorosulfonyl urea which is then saponified at 60° C. The final product is worked up and isolated according to Example 2. After drying in vacuo, there are obtained 25 parts of 2-nitrophenyl urea having a melting point of from 176° to 178° C.

EXAMPLE 11

33 Parts of 4-cyano-2-nitroaniline are stirred for 1 hour at 80° C. in 750 parts of toluene with 34 parts of chlorosulfonyl isocyanate. After cooling to 60° C., 50 parts of water are added to the suspension of the chlorosulfonyl urea which is then saponified at 60° C. The final product is worked up and isolated according to the specifications given in Example 2. After drying in vacuo, there are obtained 36 parts of 4-cyano-2-nitrophenyl urea having a melting point of from 205° to 207° C.

What is claimed is:

1. A compound of the formula

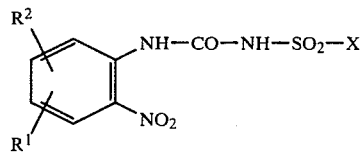

wherein X is fluorine or chlorine, $R^1$ is hydrogen or nitro, and $R^2$ is hydrogen, fluorine, chlorine, bromine, lower alkyl, lower alkoxy, trifluoromethyl, cyano, phenyl or a benzene ring fused to the substituted benzene ring.

2. A compound as claimed in claim 1, wherein X is chlorine and $R^2$ is hydrogen, chlorine, methyl, methoxy, cyano or a benzene ring fused to the substituted benzene ring.

3. A compound of the formula

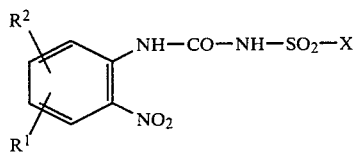

wherein X is fluorine or chlorine, $R^1$ is hydrogen or nitro and $R^2$ is hydrogen, fluorine, chlorine, bromine, lower alkyl, lower alkoxy, trifluoromethyl, cyano or phenyl.

4. A compound which is an N-o-nitro-naphthyl-N'-halogensulfonyl urea of the formula

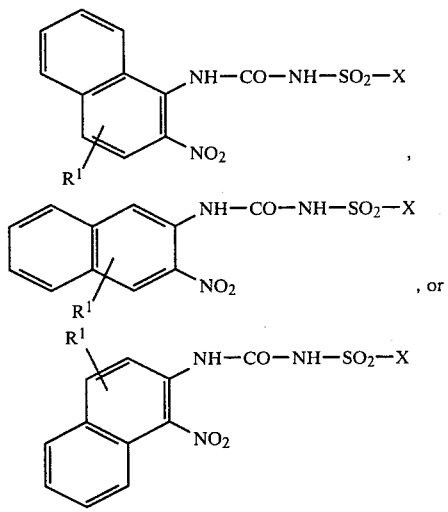

wherein X is fluorine or chlorine and $R^1$ is hydrogen or nitro.

* * * * *